United States Patent [19]

Koukos

[11] Patent Number: 5,201,657

[45] Date of Patent: Apr. 13, 1993

[54] DENTAL PROSTHESIS AND METHOD OF MANUFACTURE

[76] Inventor: Theodore J. Koukos, 10 Savin Park, West Haven, Conn. 06516

[21] Appl. No.: 840,806

[22] Filed: Feb. 25, 1992

[51] Int. Cl.$^5$ .................... A61C 11/00; A61C 13/00
[52] U.S. Cl. ................................ 433/213; 433/167
[58] Field of Search ............ 433/213, 167, 218, 219, 433/223

[56] References Cited

U.S. PATENT DOCUMENTS

| | | | |
|---|---|---|---|
| 3,937,773 | 2/1976 | Huffman | 433/213 |
| 4,078,310 | 3/1978 | Horger, Jr. | 433/213 |
| 4,721,464 | 1/1988 | Roden et al. | 433/74 |
| 4,767,331 | 8/1988 | Hoe | 433/213 |
| 4,917,347 | 4/1990 | Fenick | 433/213 |
| 4,943,237 | 7/1990 | Bryan | 433/213 |

Primary Examiner—Gene Mancene
Assistant Examiner—Cindy A. Cherichetti
Attorney, Agent, or Firm—John J. Tomaszewski

[57] ABSTRACT

Dental prostheses and a method for manufacturing dental prostheses is disclosed wherein the prosthesis formed requires substantially no bite adjustment by the dentist. This is accomplished by adjusting the height of the prosthesis die relative to the height of the other teeth when the prosthesis is being formed in a device such as an articulator.

4 Claims, 2 Drawing Sheets

DENTAL PROSTHESIS AND METHOD OF MANUFACTURE

BACKGROUND OF INVENTION

This invention relates to the field of prosthetic dentistry and, more particularly, to a method for making prosthetic devices such as crowns and bridges which require substantially no bite adjustment when the device is installed.

For simplicity, the following description will be directed to tooth crowns and their manufacture although it will be understood that this invention does apply to other dental appliances such as bridges.

A dental crown is one of the most important restorations in dentistry and it is very important that the bite of the crown when installed be as perfect as possible to minimize the amount of bite adjustment needed to be performed by the dentist. Bite adjustment is commonly performed by grinding the crown and is of discomfort to the patient, time consuming for the dentist and may even limit the life and usefulness of the crown depending on the extent of the grinding necessary.

SUMMARY OF THE INVENTION

The present invention provides a dental prosthesis and a method for manufacturing the dental prosthesis, which when installed in the patient's mouth requires substantially no bite adjustment by the dentist.

Basically, the method comprises specially preparing the die or mold from which the prosthesis will be cast by adjusting its length (height) to be less than the normal height for the crown as measured using for example an articulator. It has been found that if the height of the crown is decreased by, e.g., less than about 20 mil or more, the bite of the crown as installed will require little or no bite adjustment.

Although there are many methods of forming dental prostheses, this invention will be described in relation to one customary method with the understanding to those skilled in the art that the method may be used for other methods of making dental prostheses.

DETAILED DESCRIPTION OF THE INVENTION

Figure 1:
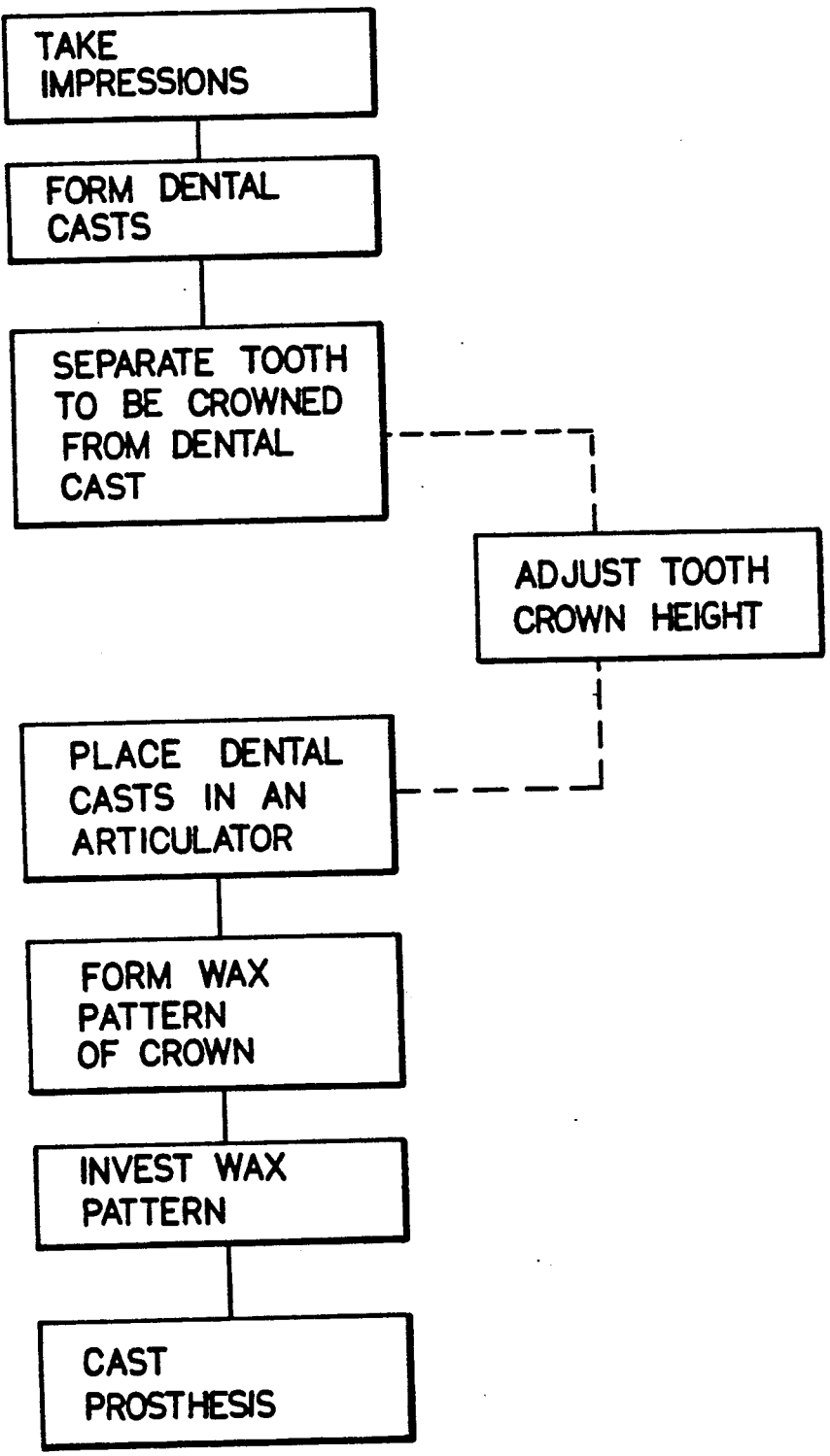
FIG. 1 is a block diagram showing the basic steps in the construction of a crown using conventional techniques, with the inventive step shown using dotted lines.
Figure 2A:
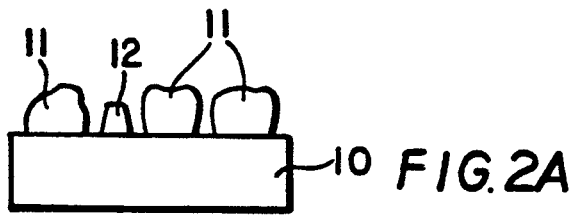
FIGS. 2A-2E show how the method of the invention is employed to form the wax pattern of the crown.
Figure 2B:
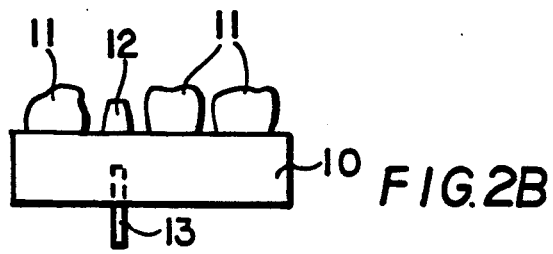
Figure 2C:
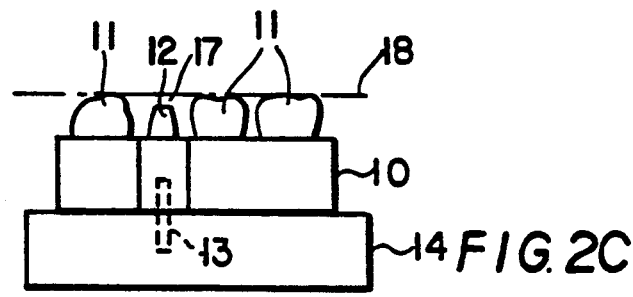
Figure 2D:
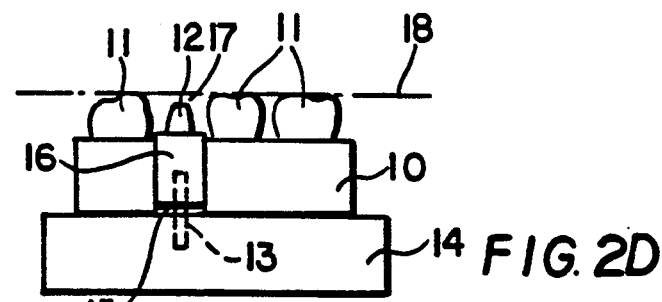
Figure 2E:
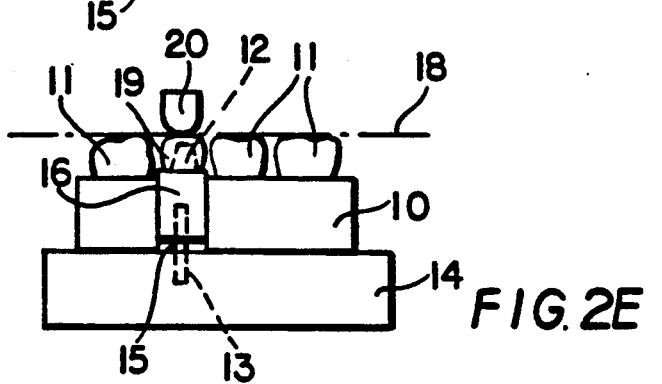

When a patient has a tooth which is to be fitted with a crown either because the tooth is badly decayed, or a portion thereof was broken away because of an injury, the dentist removes a portion of the tooth over the entire circumference in most cases, and also the occlusal surface, to leave a central post which bevels outward near the gum line. The actual steps in the fabrication and fitting of a crown commence after preparation of the tooth to be crowned or repaired.

As shown in the figures, the first step is to take impressions of the patient's upper and lower dental arches in a suitable moldable material in impression trays. Suitable impression materials are well known in the dental art. The impressions are female molds or negative replicas of the patient's dental arches.

The second step is to form dental casts 10 which are positive replicas of the patient's dental arches. The dental casts are formed of a gypsum material having good dimensional stability in order to form accurate replicas. The dental casts 10 are formed from the impressions taken above and each tooth may be called a die or stone. As shown in FIG. 2, teeth 11 and central post 12 to which the crown will be attached are on dental cast 10. Only the bottom cast is shown. Normally, the base of cast 10 is ground smooth and then pin 13 inserted for the central post 12—FIG. 2, Step B. Another cast 14 is employed to hold dental cast 10 and pin 13.

Figure 3:
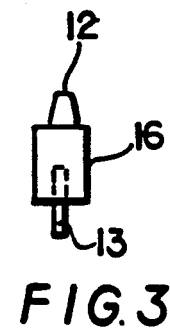
FIG. 3 shows the die or mold for the tooth to be crowned.

The die for the individual tooth 12 to be crowned from dental cast 10 is then separated as shown in FIG. 2—Step C by fine saw blades to allow easy manipulation of the die and then trimmed, i.e. ditched, such that the margins (the exact point where the crown is to end) are visible and accessible, all as well known in the dental art. The separated crown die 16 is shown in FIG. 3.

The dental casts 10 and 14 and the corresponding upper castings (not shown) are next mounted in an articulator in a manner to have the casts, 10 and 14 (both upper and lower) in their centric occlusal position; that is, the teeth on the dental casts are in the same relative position as the teeth in the patient's mouth. For illustrative purposes only, it will be assumed that a lower bicuspid is to be crowned (shown as 12); hence, there will be a gap 17 between the lower bicuspid to be crowned and its mating upper bicuspid—shown by line 18 which represents the mating point (level) for the lower and upper teeth.

Figure 4A:
FIG. 4 shows a device used to adjust the height of the crown to be made by the method of the invention.
Figure 4B:
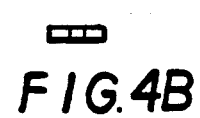

It is at this step of the method where the inventive step is employed. Thus, the gap 17 between the lower bicuspid to be crowned and its mating upper bicuspid is decreased by, e.g., inserting a thin material, e.g., metal foil 15 (FIG. 4) between the base of the die 16 and the casting 14. This may conveniently be done using a thin metal foil, e.g., of less than about 20 mil and having a hole therein to accept the pinned die. A preferred thickness of the foil is about 1–10 mil, with a highly preferred thickness being 1–6, e.g., 3 mil. As can be seen from FIG. 2, Step D, this invention has the effect of raising die 16 relative to the teeth 11 in dental cast 10 and decreasing gap 17.

The next step, FIG. 2, Step E, is to form a wax pattern of the crown 19 to be fabricated over tooth 12 using standard techniques. The wax pattern is constructed on the replica of the prepared tooth 12 on the lower dental cast. The outside of the wax pattern is shaped to fit the adjacent lower teeth, while the inside portion of the wax is contiguous with the prepared surface of the tooth. The occlusal surface on the wax pattern is formed to fit the cusps on the mating upper bicuspid (to meet line 18—and upper tooth 20). It is thus noted that the material removed in preparation of tooth to be restored has been replaced with wax. Theoretically at least, if the crown 19 can be built to the exact shape and size of the wax pattern, when the crown is cemented in place, the restored tooth will now fit as did the original tooth.

The next step is to very carefully remove the wax pattern including die 16 from the lower dental cast and to invert it in a refractory material. The refractory material is usually a material which has been specially formulated to withstand the thermal shock of sudden exposure to high temperature molten metal. A sprue is formed of wax and joined to the wax pattern. The sprue forms the passage through which the wax pattern is evaporated, and also the passage through which the molten metal enters the cavity formed by the evaporated wax pattern. After the refractory material has set, the assembly is heated to about 900 degrees F. which will vaporize the wax and leave a cavity mold which is a negative replica of the crown to be cast in the next step below. It is noted that the outside of the cavity mold is comparable to the outside configuration of the desired crown, and that there is an inner portion which is comparable to the prepared surface of the tooth 12 extending downward into the cavity mold.

The next step is to mount the refractory mold in a centrifugal casting machine such as is used in most dental laboratories. An alloy slug is heated to the proper temperature and the molten alloy is shot into the mold where it is allowed to harden and cool down. At the proper time the refractory material is broken away from the cast crown. After the rough crown has been removed, it is cleaned and polished and ready to be installed.

It is to be understood that the embodiments of the present invention as shown and described are to be regarded merely as illustrative, and that the invention is susceptible to variations, modifications and changes without regard to construction methods, within the scope of the appended claims.

I claim:

1. A method for manufacturing a dental prosthesis comprising:
    (a) forming dental castings of upper and lower impressions of teeth taken in a patient's mouth;
    (b) preparing a die of the tooth or teeth from the casting for which the prosthesis is desired so it can be removed and replaced in the casting, the die having an upper part containing the tooth or teeth for the prosthesis and a lower base;
    (c) mounting the dental castings containing the die in a dental articulator or other such device;
    (d) inserting a thin material between the base of the die and the dental casting to raise the die relative to the teeth in the dental casting;
    (e) forming a pattern of the desired tooth configuration over the tooth portion of the die as determined by the articulator or other such device;
    (f) removing the pattern and casting the prosthesis.

2. The method of claim 1 wherein the thin material is less than 20 mil thick.

3. The method of claim 2 wherein the thickness of the thin material is between about 1-10 mil.

4. The method of claim 3 wherein the thickness of the thin material is between about 1-6 mil.

* * * * *